(12) United States Patent
Wong

(10) Patent No.: US 7,335,885 B2
(45) Date of Patent: *Feb. 26, 2008

(54) ULTRA LOW POWER NDIR GAS SENSOR FIRE DETECTOR

(75) Inventor: Jacob Y. Wong, Goleta, CA (US)

(73) Assignee: Airwave, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/367,440

(22) Filed: Mar. 3, 2006

(65) Prior Publication Data

US 2007/0114412 A1 May 24, 2007

Related U.S. Application Data

(63) Continuation-in-part of application No. 11/284,460, filed on Nov. 21, 2005.

(51) Int. Cl.
*G01J 1/00* (2006.01)
(52) U.S. Cl. ............... 250/339.15; 340/328; 340/627; 340/629; 250/339.06; 250/339.03; 250/339.12
(58) Field of Classification Search ........... 250/339.15, 250/339.3, 339.06, 339.03, 339.01, 339.12; 340/627, 328, 629
See application file for complete search history.

(56) References Cited

U.S. PATENT DOCUMENTS 5,721,430 A * 2/1998 Wong .................... 250/339.13
5,800,360 A * 9/1998 Kisner et al. ............... 600/532
5,966,077 A * 10/1999 Wong ......................... 340/630
6,166,647 A * 12/2000 Wong ......................... 340/628
2005/0092067 A1* 5/2005 Petrovic et al. ............ 73/31.05

* cited by examiner

*Primary Examiner*—David Porta
*Assistant Examiner*—Djura Malevic
(74) *Attorney, Agent, or Firm*—Wagner, Anderson & Bright, LLP; Roy L. Anderson

(57) ABSTRACT

A fire detector and method for generating an alarm signal in response to a fire uses an NDIR sensor to generate a detector signal based upon one or more absorption bands selected from the 15.1μ absorption band of CO2, the 6.27μ absorption band of H2O and the 4.67μ absorption band for CO and generates an alarm signal when a signal processor receives the detector signal and a preselected criterion is met that is indicative of the onset of a fire based upon an analysis of the detector signal using a detection algorithm that relies upon a trending pattern of the detector signal such as recognizing a substantial drop in the detector signal strength. The fire detector has a waveguide sample chamber (which can be of a re-entrant design) with at least one opening covered by a thin filtering membrane and a heat exchanger thermally connected to the sample chamber with at least one opening covered by another thin filtering membrane. If the NDIR sensor is to detect H2O molecules, the filtering membrane on the heat exchanger (which can be integrally formed out of aluminum with the sample chamber) allows H2O molecules to pass through it and inside surfaces of both the sample chamber and the heat exchanger are coated with a hydrophobic coating to prevent condensation of H2O molecules.

13 Claims, 6 Drawing Sheets

A drawing showing schematically the design and implementation of an ultra low power NDIR gas sensor deployed as a fire detector

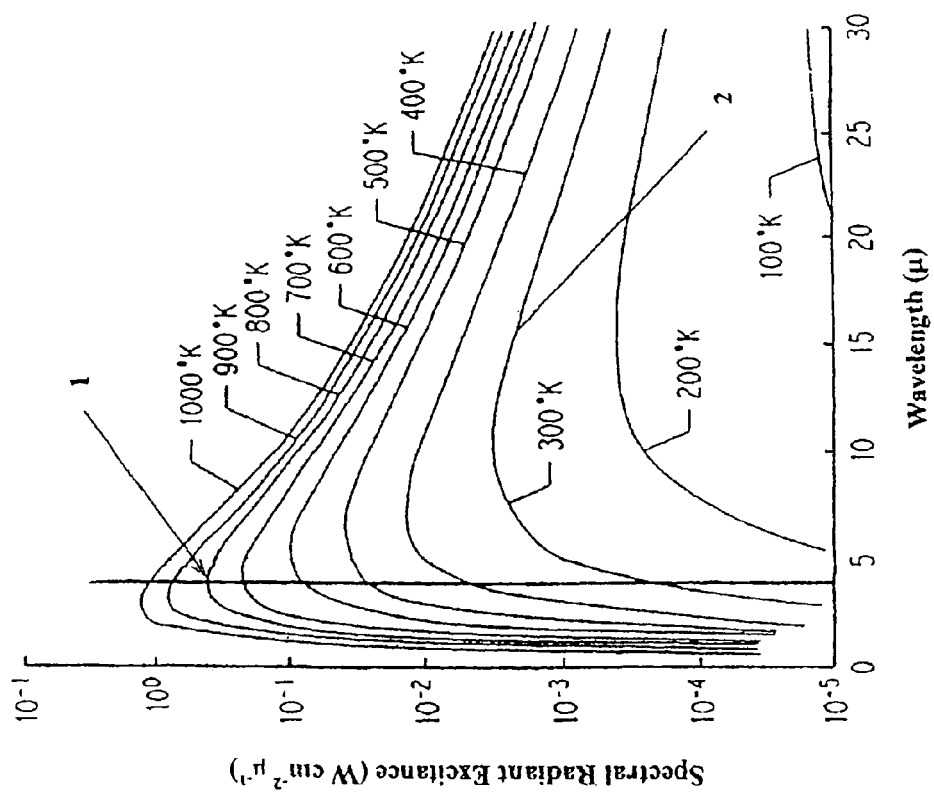
Figure 1. A graph showing the spectral radiant excitance of a blackbody source at temperatures 100 - 1,000 °K.

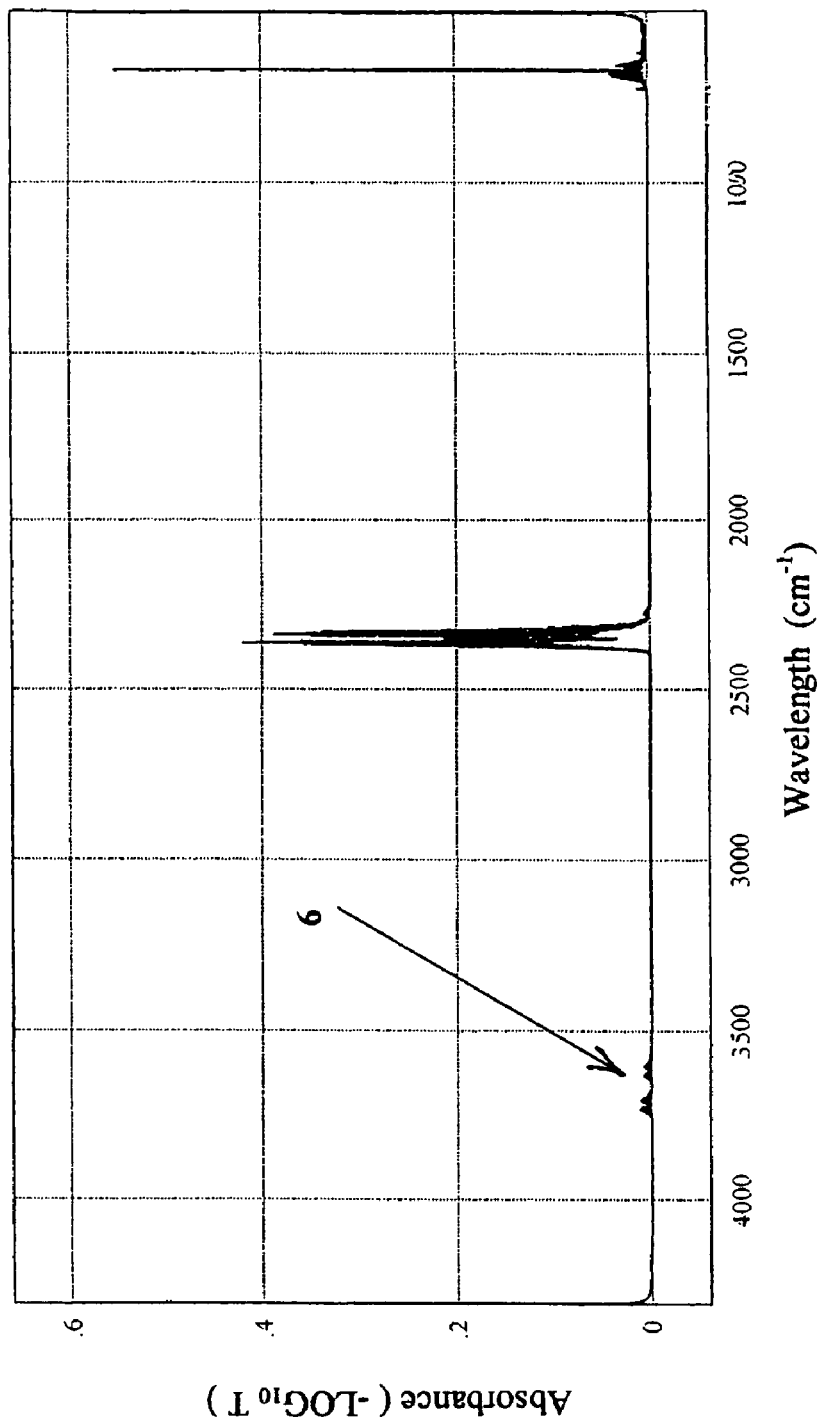
Figure 2. A graph showing the absorbance of CO2 gas at wavelengths from ~2 μ - 20 μ (5,000 cm⁻¹ - 500 cm⁻¹). Only the 4.26 μ and ~15 μ absorption bands of CO2 are shown to be prominently present in this spectral region.

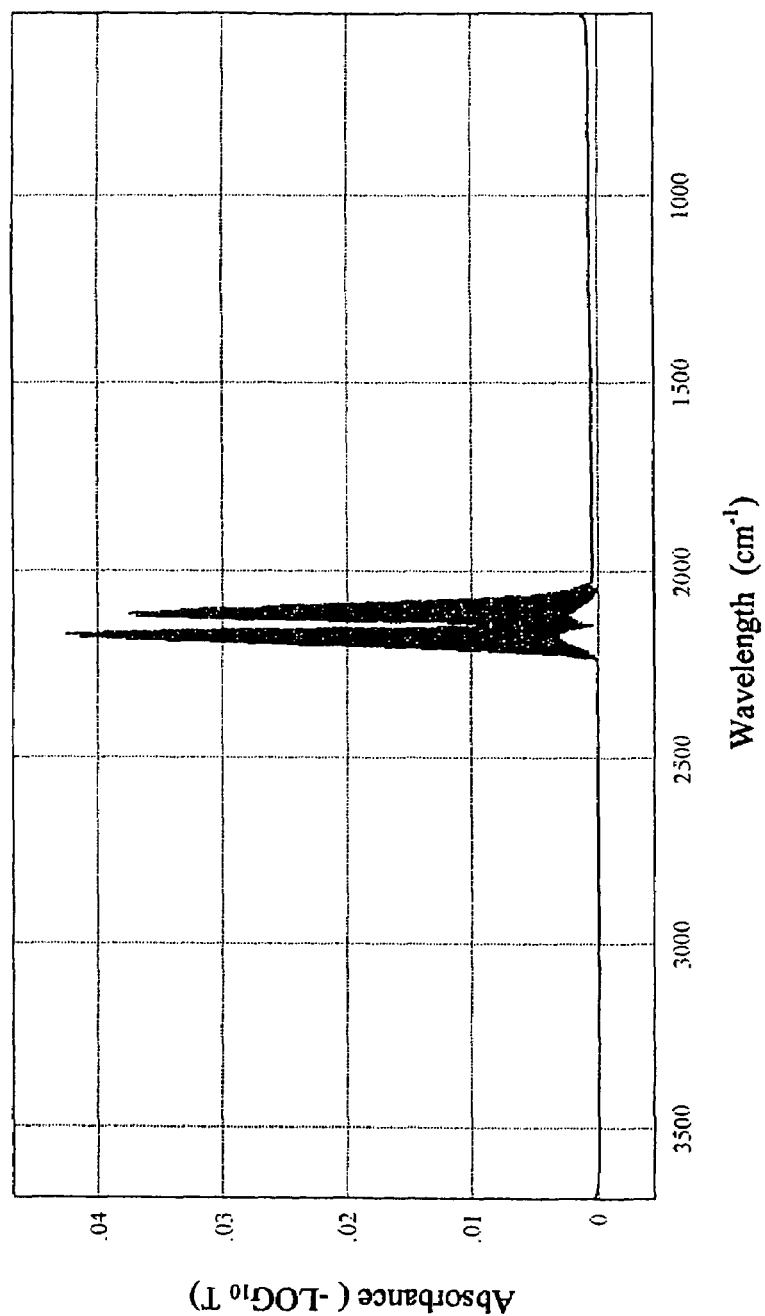
Figure 3  A graph showing the absorbance of Carbon Monoxide (CO) gas at wavelengths from ~2 μ - 20 μ (5,000 cm-1 - 500 cm-1) showing an absorption band at 4.65 μ.

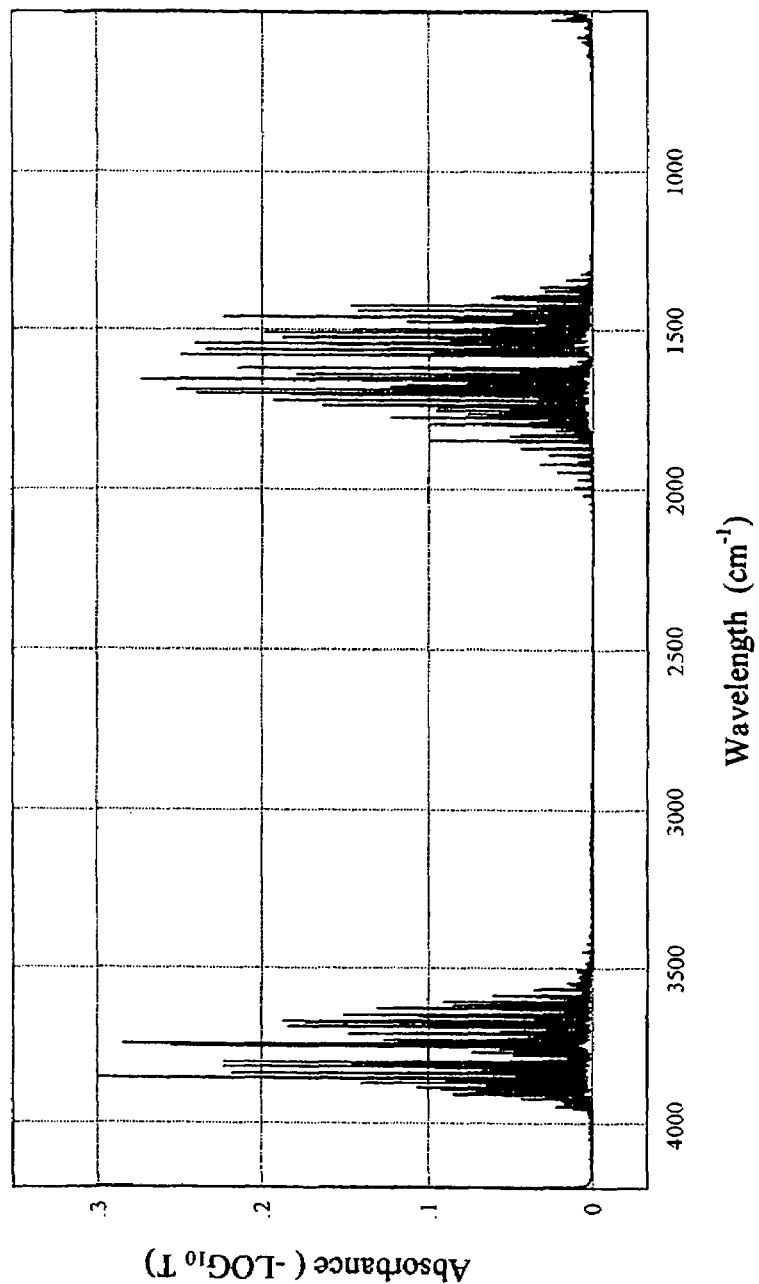
Figure 4. A graph showing the absorbance of water vapor (H2O) at wavelengths from ~2 μ - 20 μ (5,000 cm-1 - 500 cm-1) showing the strong absorption bands at 2.67 μ and 6.27 μ.

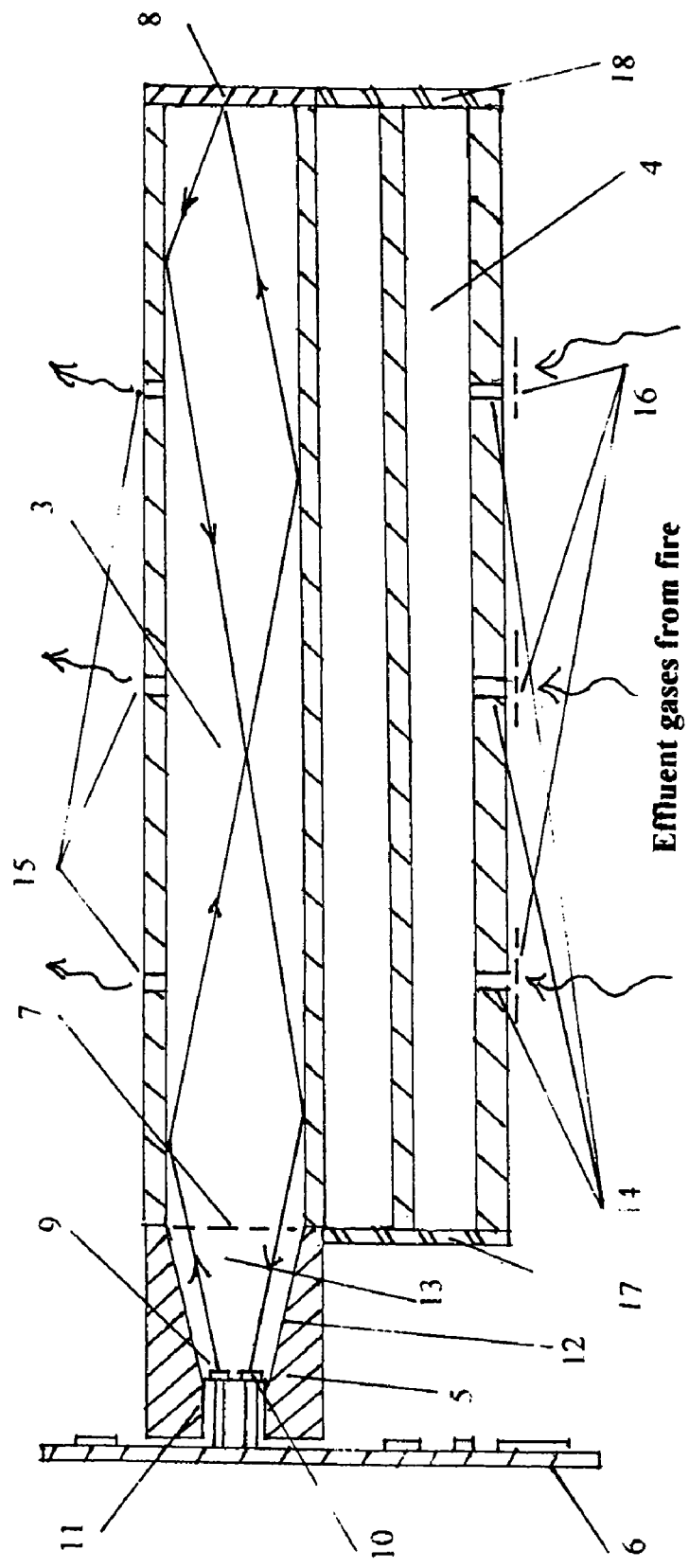
Figure 5. A drawing showing schematically the design and implementation of an ultra low power NDIR gas sensor deployed as a fire detector

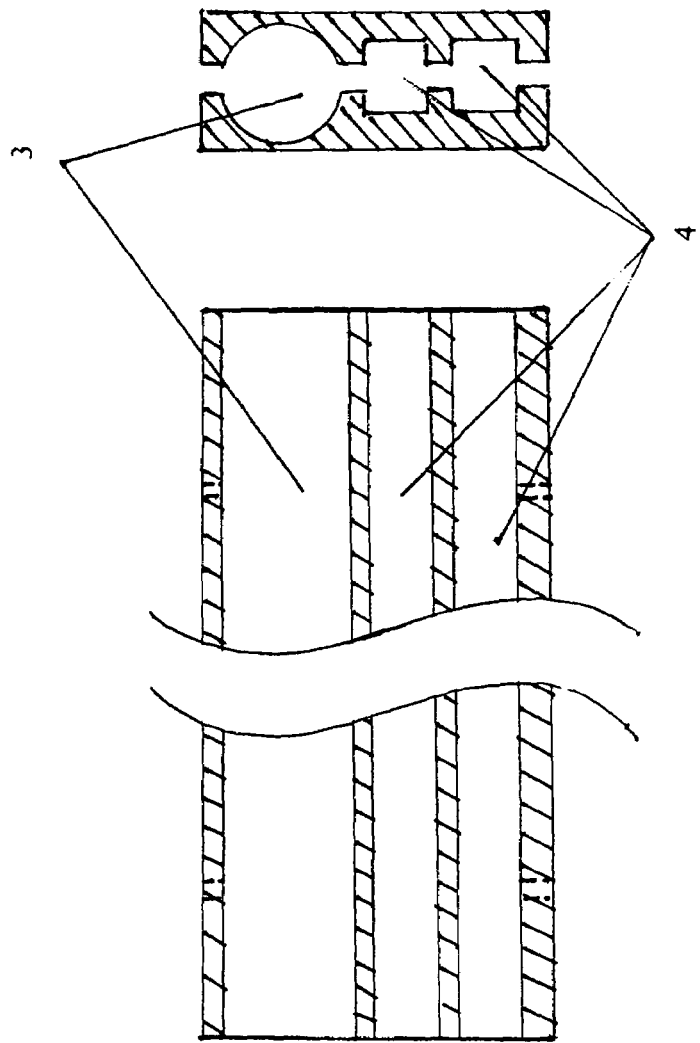
Figure 6. A drawing showing the cross-section for the unit-body sample chamber and heat exchanger design of the fire detector as portrayed in Figure 5.

ULTRA LOW POWER NDIR GAS SENSOR FIRE DETECTOR

CROSS-REFERENCE TO RELATED APPLICATIONS

This application is a continuation-in-part of U.S. Ser. No. 11/284,460 filed Nov. 21, 2005, entitled "Ultra Low Power NDIR $CO_2$ Gas Sensor Fire Detector," the disclosure of which is specifically incorporated herein by reference.

FIELD OF THE INVENTION

The present invention is in the field of gas analysis and more particularly relates to an ultra low power gas sensor designed to be used as a compact, reliable, low cost, fast responding and false alarm resistant fire detector.

BACKGROUND OF THE INVENTION

The Non-Dispersive Infrared ("NDIR") technique has long been considered as one of the best methods for gas measurement. In addition to being highly specific, NDIR gas analyzers are also very sensitive, stable, reliable and easy to maintain. The major drawback of the NDIR gas measurement technique has been its relatively expensive implementation and high power consumption.

Ever since the NDIR technique of gas measurement was first introduced and practiced in the mid 1950's, a large number of improved measurement techniques based upon the NDIR principle for gas detection have been proposed and successfully demonstrated. The most notable advances over the years in this field are summarized as follows.

Burch et al. (U.S. Pat. No. 3,793,525) and Blau et al. (U.S. Pat. No. 3,811,776) in 1974 were the first to advance a so-called "Double Beam" technique for NDIR gas measurement by taking advantage of the principle of nonlinear absorption for some strongly absorbing gases such as $CO_2$ to create a reference channel. Shortly thereafter, this "Double Beam" NDIR gas sensor technique was greatly simplified with the use of two interposed spectral filters (one absorbing and one neutral) to create a sample and a reference detector channel. Subsequent NDIR gas sensors, designed using this technique, have enjoyed good output stability as a function of time.

In U.S. Pat. No. 4,578,762 (1986) Wong advanced the first self-calibrating NDIR $CO_2$ analyzer using a novel two-wheel chopper and mirror arrangement. Another improved type of such gas analyzer is shown and described in U.S. Pat. No. 4,694,173 (1987) by Wong. This gas analyzer has no moving parts for effecting the interposition of spectral filters or absorbing and non-absorbing cells to create both a sample and reference detector channel as in the NDIR gas analyzers described earlier.

In U.S. Pat. No. 5,163,332 (1992), Wong advanced the so-called "wave-guide" sample chamber for simplifying NDIR gas sensors into ones that are compact, rugged and low-cost while still maintaining their superior performance characteristics.

All of the NDIR gas analyzers described above for the measurement of the concentrations of one or more gases in a mixture perform well functionally and have contributed overwhelmingly to the overall technical advancement in the field of gas analysis during the past two decades. They have been widely accepted in both the medical and industrial communities. Despite their undisputed success over the years, there still remains an important application, namely the commonplace household fire detector, not successfully realized to date due to the fact that NDIR gas sensors are sill too costly and consume too much power when used as sentinel fire detectors.

A majority of fire detectors in use today in almost all public buildings and private dwellings are in essence smoke detectors as they only detect the smoke resulting from a fire. The most common smoke detectors currently in use belong to two types. The first type is the so-called ionization smoke detector best for detecting invisible smoke particles ranging in size from <1.0 microns to ~5 microns. The second type is called the photoelectric smoke detector best for detecting visible smoke particles >5 microns in size. For the past two decades, the ionization smoke detectors because of their low cost (<$10 retail) have dominated the fire market and are in use in over 90% of households. In recent years, photoelectric smoke detectors, because of their higher cost (<$30 retail), have fallen significantly behind in sales. Combined ionization and photoelectric smoke detectors, albeit at an even higher cost (~$40 retail), have also been available for quite sometime but have not to date received much acceptance by the public.

Despite their low cost, relatively maintenance-free operation and wide acceptance by the buying public, the smoke detectors in widespread use today are not without problems and certainly are far from being ideal. One of the biggest problems with ionization smoke detectors besides being radioactive (Americium-241) is their frequent false-alarm. By the nature of its operational principle, any micron-size particulate matter other than smoke from an actual fire can set off the alarm. Kitchen grease particles generated by a hot stove is one classic example. Over-zealous dusting of objects and/or furniture near the detector is another. Frequent false-alarms are not just a harmless nuisance; some people actually disable their smoke detectors by temporarily removing the battery in order to escape such annoying episodes. This latter situation could be outright dangerous especially when these people forget to rearm their smoke detectors.

Another significant drawback for the current ionization smoke detector is its relatively slow speed to alert people of a fire. There are several factors that contribute to this particular drawback. The first fact is the detector trigger threshold for smoke which directly affects its response time to the onset of a fire. No doubt a lower trigger threshold would mean a faster fire detector. However, it also means more frequent annoying false alarms for the user. The second factor is the particular placement of the detector with respect to the spot where fire breaks out. Unlike ordinary gases, smoke is actually a complex sooty molecular cluster that consists mostly of carbon. It is much heavier than air and thus diffuses much slower than the gases we encounter everyday. Therefore, if the detector happens to be at some distance from the location of the fire, it will be awhile before enough smoke gets into the sampling chamber of the smoke detector to trigger the alarm. A third factor is the nature or type of the fire itself. Although smoke usually accompanies fire, the amount produced can vary significantly depending upon the composition of the material that catches fire. For example, oxygenated fuels such as ethyl alcohol and acetone give less smoke than the hydrocarbon from which they are derived. Thus, under free-burning conditions oxygenated fuels such as wood and polymethylmethacrylate give substantially less smoke than hydrocarbon polymers such as polyethylene and polystyrene. As a matter of fact, a small number of pure fuels, namely carbon monoxide, formaldehyde, metaldehyde, formic acid and methyl alcohol, burn with non-luminous flames and do not produce smoke at all.

Since fire is an oxidation process, detection of a sudden increase in ambient levels of one or more of the three principal effluent gases of fire, namely $CO_2$, $H_2O$ and Carbon Monoxide (CO) could be an effective way of detecting same. For the past 20 years, the use of $CO_2$ sensor as a standalone fire detector or in combination with smoke detectors has been continually advocated by experts as the most effective fire detector. The reason is two-fold. First, there is a significant advantage of using a $CO_2$ sensor rather than a smoke detector for fire initiation detection. The mobility of $CO_2$ as a gas is far greater than that for smoke which is much heavier. Therefore $CO_2$ diffuses from the fire to the detector in a much shorter time leading to a faster response time for enunciating fire. Second, over the past two decades, compact, low cost and reliable NDIR type $CO_2$ sensors have become readily available. As a matter of fact, over the same period of time, a large number of deployment schemes, fire fighting techniques and fire control strategies, which use either a standalone NDIR $CO_2$ sensor or in combination with smoke detectors, have been advanced. The most notable proposals of such are summarized as follows.

In U.S. Pat. No. 5,053,754 (1991), Wong advanced the first NDIR $CO_2$ sensor used as a standalone fire detector. A fire detection system using at least two NDIR $CO_2$ sensors positioned at spaced locations in an area for pin-pointing the exact origin of a fire was described in U.S. Pat. No. 5,079,422 (1992) by Wong. Meanwhile a standalone and compact low-cost fire detector which responds quickly to an increase in the concentration of $CO_2$ gas in the ambient air was advanced in U.S. Pat. No. 5,103,096 (1992) by Wong. In U.S. Pat. No. 5,369,397 (1994), an adaptive fire detector taking advantage of the capability of an NDIR $CO_2$ sensor for computing the rate of $CO_2$ increase to shorten the response time for enunciating the onset of a fire was also advanced by Wong. In U.S. Pat. No. 5,592,147 (1997), an NDIR $CO_2$ sensor used cooperatively in combination with a photoelectric smoke detector for significantly reducing false alarms was put forth by Wong. Also in 1997 and in U.S. Pat. No. 5,691,704, Wong disclosed another NDIR $CO_2$/photoelectric smoke detector combination fire detector with special software which can be designed into a single semiconductor chip for cost reduction and further false alarm improvement. In U.S. Pat. No. 5,767,776 (1998), Wong disclosed the design of an NDIR $CO_2$ and smoke detector combination which reduces the maximum average response time to less than 1.5 minutes. Further refinement of this design was described in U.S. Pat. No. 5,798,700 (1998) by Wong, U.S. Pat. No. 5,945,924 (1999) by Marman et al. and U.S. Pat. No. 5,966,077 (1999) by Wong. Finally, a method for dynamically adjusting criteria for detecting fire through smoke concentration using an NDIR $CO_2$ and smoke detector combination was described by Wong in U.S. Pat. No. 6,107,925 (2000).

Despite the continual and persistent advocacy of many fire experts that an NDIR $CO_2$ sensor, either as a standalone fire detector or in combination with a smoke detector, is better than present-day smoke detectors in both speed of response and resistance against false alarms, it has yet to be exploited as a superior fire detector. The reasons are two-fold. First, even with the drastic cost reduction for present-day NDIR $CO_2$ sensors, the cost is still far too high when compared with ionization type smoke detectors. Second and by far the most significant is the fact that being an NDIR gas sensor, its active infrared source uses far too much power when operated continuously. Because of this, it is not suitable for use in almost any circumstance, whether it is residential, commercial or industrial.

In an earlier related application cross referenced above, U.S. Ser. No. 11/284,460 filed Nov. 21, 2005, to overcome these problems, a novel design for an NDIR $CO_2$ sensor fire detector was disclosed aimed at further lowering its cost and, more importantly, reducing its power consumption so that it uses just as little power as an ionization smoke detector. It is an object of the present application to extend this design methodology to include the other two effluent gases generated by a fire, namely water vapor or $H_2O$ and Carbon Monoxide (CO) in addition to $CO_2$, for achieving similar NDIR gas sensor fire detectors. Furthermore, a better NDIR gas sensor fire detector design along with accompanying fire enunciation algorithms for improving the performances of such fire detectors are advanced.

SUMMARY OF THE INVENTION

The present invention is generally directed to a fire detector that uses an NDIR sensor that generates a detector signal based upon at least one absorption band selected from the a 15.1µ absorption band of $CO_2$, a 6.27µ absorption band of H2O and a 4.67µ absorption band for CO and generates an alarm signal to warn of a fire when a signal processor receives the detector signal and a preselected criterion is met.

In a first, separate group of aspects of the present invention, the signal processor relies upon a detection algorithm that is based upon a sudden drop of the detector output signal (e.g., when the drop is greater than 20%) indicative of the onset of a fire. The signal processor can utilize synchronized signal processing from the detector signal and rely upon a detection algorithm that is based upon a synchronized output signal representative of the concentration of one or more of the gasses of CO, $CO_2$ and $H_2O$ and can be based upon two or more of the absorption bands of 15.1µ for $CO_2$, 6.27µ for $H_2O$ and 4.67µ for CO.

In a second, separate group of aspects of the present invention, the NDIR sensor (which can be used in a standalone smoke detector or combined with a smoke detector) has a waveguide sample chamber (which can be of a re-entrant design) with at least one opening covered by a thin filtering membrane (such as polyethylene) that allows $CO_2$ and $H_2O$ molecules to diffuse freely into and out of the sample chamber but rejects dust and smoke particles from entering the sample chamber, a heat exchanger thermally connected to the sample chamber with at least one opening covered by another thin filtering membrane that allows preselected molecules to diffuse freely into and out of the heat chamber but rejects dust and smoke particles from entering the heat exchanger, and an infrared components assembly that houses an infrared source and a detector which is thermally coupled to an end of the sample chamber. If the NDIR sensor is to detect $H_2O$ molecules, the filtering membrane on the heat exchanger (which can be integrally formed out of aluminum with the sample chamber) allows $H_2O$ molecules to pass through it and inside surfaces of both the sample chamber and the heat exchanger are coated with a hydrophobic coating to prevent condensation of $H_2O$ molecules. Also, a condensing optical mirror in front of the source and detector of the NDIR sensor can be used to enhance the re-entrant radiation flux collected at the detector.

In a third, separate group of aspects of the present invention, a method for generating an alarm signal in response to a fire is based upon using an NDIR sensor to generate a detector signal based upon one or more of the three absorption bands of 15.1μ for $CO_2$, 6.27μ for $H_2O$ and 4.67μ for CO and generating the alarm signal when a preselected criterion indicative of the onset of a fire is met based upon an analysis of the detector signal. The analysis of the detector signal can be performed by using a detection algorithm that relies upon a trending pattern of the detector signal such as a substantial drop in the detector signal strength when a species that is the subject of the chosen absorption band(s) subsequently arrives near the sensor as the fire persists.

It is therefore an object of the present invention to advance a new design for an NDIR gas sensor aimed at further lowering its cost and, more importantly, reducing its power consumption so that it uses approximately the same power as an ionization detector. It is a further object of the present invention to design such an NDIR gas sensor that is suitable for use as a low cost, false alarm resistant and fast response fire detector.

These and further objects and advantages will be apparent to those skilled in the art in connection with the drawings and the detailed description of the invention set forth below.

BRIEF DESCRIPTION OF THE DRAWINGS

FIG. 1 is a graph showing the spectral radiant excitance of a blackbody source at temperatures 100-1,000° K.

FIG. 2 shows the absorbance of $CO_2$ gas at wavelengths from ~2μ-20μ (5,000 cm–1-500 cm–1). Only the 4.26μ and 15.1μ absorption bands of $CO_2$ are shown to be prominently present in this spectral region.

FIG. 3 shows the absorbance of Carbon Monoxide (CO) gas at wavelengths from ~2μ-20μ (5,000 cm–1-500 cm–1) showing an absorption band at 4.67μ.

FIG. 4 shows the absorbance of $H_2O$ at wavelengths from ~2μ-20μ (5,000 cm–1-500 cm–1) showing strong absorption at 2.67μ and 6.27

FIG. 5 shows schematically the design and implementation of an ultra low powered NDIR gas sensor deployed as a fire detector.

FIG. 6 shows the details for the cross-section for the unit-body sample chamber and heat exchanger design of the fire detector as portrayed in FIG. 5.

DETAILED DESCRIPTION OF THE INVENTION

Over the past three decades, the design of NDIR $CO_2$ gas sensors has invariably used the strong $CO_2$ infrared absorption band at 4.26μ. This band is not only strong, it is also very specific. In other words, no other gases, other than some extremely weak water vapor absorption continuum, have absorption bands within it. Thus, interferences caused by the presence of other gases to the $CO_2$ measurement using this band are virtually nonexistent. Because of these facts, NDIR $CO_2$ sensors are not difficult to design and they were among the earliest NDIR gas sensors manufactured and available for sale to the public circa around mid 1950's.

In accordance with conventional wisdom for NDIR sensor design, the most optimum infrared source to use for $CO_2$ detection should have a blackbody temperature at around 800-900° K, which has its peak spectral radiant excitance located at around 4.26μ according to Planck's Radiation Law as shown in FIG. 1. FIG. 1 shows the graph depicting the spectral radiant excitance of a blackbody source at temperatures 100-1,000° K. The peak spectral radiant excitance for a 800° K blackbody is at 4.26μ which is also the center wavelength (CWL) for the 4.26μ absorption band of $CO_2$ as indicated by the vertical line 1. This confirms the fact that the optimum temperature of the an infrared source using the 4.26μ absorption band for designing an NDIR $CO_2$ sensor is ~800° K. However, the use of such a high temperature infrared source for the design of a NDIR $CO_2$ sensor using the 4.26μ absorption band is the main reason why the power consumption for such a sensor is invariably so high and cannot be easily lowered. Since most fire detectors have always been battery-operated, requiring very low power consumption for their continuous operation, this is also the principal reason why NDIR $CO_2$ sensors to date have not been used as fire detectors.

Also shown in FIG. 1 is the Planck's radiation curve for a 300° K blackbody 2, which has a peak spectral radiant excitance at ~10-15μ centering approximately on the 15μ absorption band of $CO_2$. This is the reason why a much lower temperature infrared source can be used just as efficiently for the design of an NDIR $CO_2$ sensor when one uses the 15μ absorption band of $CO_2$ as disclosed in my earlier application (cross-reference "Ultra Low Power NDIR $CO_2$ Gas sensor Fire Detector").

Although water vapor and CO are also principal effluent gases from a fire, detection of their sudden increased presence is seldom used as a means to signal the onset of a fire. There are several reasons to explain this. Let us start off with CO. CO is invariably generated in a lesser quantity than $CO_2$ at the beginning of combustion which is an oxidation process unless the latter is very sluggish (slow burning or incomplete combustion), like in a smoldering fire. However, once the combustion or fire takes hold with oxidation being the primary process, there is far more $CO_2$ being produced than CO. It is only when the fire temperature reaches ~600° C. or above that more CO is produced at the expense of forming $CO_2$ and Carbon. Since normally the CO concentration is very low at home or at work (~a few ppm), the sudden increase of CO concentration above a certain threshold, say 20 ppm, as detected by an NDIR gas sensor, could be used to indicate the onset of a fire, though more likely to be one that is smoldering or slow-burning. Whereas NDIR $CO_2$ sensors with adequate sensitivity to detect $CO_2$ concentration level increase in a fire (+/-50 ppm's) are easy to build, it is not so for NDIR CO sensors, especially those with sensitivity of just a few ppm's. The reasons can be seen as follows.

First, the CO absorption band at 4.67μ is approximately ten times weaker than the 4.26μ $CO_2$ counterpart (see FIGS. 2 and 3). FIGS. 2 and 3 shows respectively the absorbance of $CO_2$ and CO gas at wavelengths from ~2μ-20μ (5,000 cm–1-500 cm–1). It can be seen that the strength of either the 4.26μ or the 15.1μ absorption band is ~10 times the strength of the 4.67μ counterpart. Second, there are significant amount of interferences due to adjacent $CO_2$ and $H_2O$ absorption bands that affect the CO modulation at 4.67μ which make it difficult to detect small amounts of CO, like in a few ppm's or less. Third, small, reliable and inexpensive miniature light bulbs, which can be used as very effective infrared sources to build NDIR $CO_2$ sensors using the 4.26μ band, cannot be used for CO due to the very low transmission of the light bulb glass envelop at 4.67μ. Putting all of these together, a very low-cost and high sensitivity NDIR CO gas sensor has to date not been available for purchase in the marketplace for use as a possible fire detector. Needless to say, only optical gas sensors like the NDIR type are stable enough for use as fire detectors. Relatively low cost and small electrochemical CO sensors are today readily available for purchase in the marketplace. However, unlike NDIR gas sensors, they are known to be unstable over relatively short periods of time and are therefore unsuitable for use as fire detectors.

Since almost all combustible materials contain the hydrogen atom (H) bonded covalently with carbon and Oxygen, the generation of $CO_2$ molecules during the oxidation process of a fire invariably involves also the generation of $H_2O$ molecules. This is very much likened to the metabolism of food stuff, which contains both oxygen and hydrogen atoms along with other lesser quantity molecules, inside our body. The end products of a normal or healthy metabolism are $CO_2$ and $H_2O$ plus the output of energy.

The reasons why a sudden increase in $H_2O$ concentration level has not been singled out to date for detecting the onset of a fire are also many fold despite the fact that $H_2O$ has a very strong absorption line at 6.27μ as shown in FIG. 4. First and foremost, whereas indoor $CO_2$ and CO concentrations are relatively stable, the presence of $H_2O$ in the air (indoors or out) is weather-related and can vary significantly over short periods of time. Furthermore, the concentration level can be relatively high, varying from a few thousand ppm's when the air is dry to over 50,000 ppm's when it is very wet or humid. Second, a low cost and long-term stable humidity sensor is at present simply not available for sale anywhere and therefore cannot be used as a reliable fire detector today. Third, even in the presence of a fire when $H_2O$ molecules are being abundantly produced, the concentration level of $H_2O$ might not even be measured accurately at any time by a humidity sensor due to the fact that $H_2O$ condenses readily on any cold surfaces and thereby disappears without a trace. Thus due to the peculiar behavior of $H_2O$ molecules and the lack of adequate, especially with respect to long-term stability, humidity sensors available today, a sudden increase in $H_2O$ concentration level has not been used as a means to signal the onset of a fire.

In order to overcome this seemingly untenable situation, I have, in an earlier application cross referenced above, U.S. Ser. No. 11/284,460 filed Nov. 21, 2005, advanced the idea of using an alternate absorption band for $CO_2$ in order that the operating temperature of an infrared source used for its detection can be much lower than the commonly used 4.26μ absorption band. As shown in FIG. 1, the Planck's radiation curve for a 300° K blackbody 2 has a peak spectral radiant excitance at ~10-15μ centering approximately on the 15μ absorption band of $CO_2$. This is the reason why a much lower temperature infrared source can be used just as efficiently for the design of an NDIR $CO_2$ sensor when one uses the 15μ absorption band of $CO_2$ as disclosed in my earlier application U.S. Ser. No. 11/284,460 filed Nov. 21, 2005.

The current application extends the design methodology of the ultra low power NDIR gas sensor fire detector to the use of the other two principal effluent gases generated by a fire, namely water vapor ($H_2O$) and Carbon Monoxide (CO). In parallel the present invention also advances a new design for the ultra low power NDIR gas sensor fire detector encompassing a number of improvements which are required when $H_2O$ or CO fire effluent gases are used in lieu of $CO_2$. Among the crucial improvements of this new NDIR gas sensor detector are 1) to elongate the path length of the sample chamber via the use of the re-entrant technique; 2) adding a heat exchanger adjunct to the sample chamber and keeping the inside and outside of the combined structure polished and hence relatively cool so as to reduce the effective temperature of the incoming effluent gases for more efficient detection in view of the Law of Detailed Balance; 3) adding a hydrophobic coating to the inside of the sample chamber and the heat exchanger so as to prevent the incoming $H_2O$ from the fire from condensing and hence disappearing inside same and 4) using a condensing optical mirror in front of the source and detector duo in order to enhance the re-entrant radiation flux collected at the detector and hence improve the S/N for the fire detector.

FIG. 5 shows schematically the design and implementation of the presently invented NDIR gas sensor fire detector. This design is applicable to the use of all three principal effluent gases generated by a fire with only minor modifications for each of the effluent gas used. As pointed out in the earlier application (cross-reference), one of the most important attributes of the present invention is the proper selection of the most appropriate infrared absorption bands for the gases in question in order to lower the operating temperature for the infrared source to an absolute minimum thus saving power. Therefore for the $CO_2$ gas, the 15.1μ band is used in lieu of the 4.26μ one. For the $H_2O$ gas, the 6.27μ band is used instead of the 2.67μ one whereas for the CO gas, we have only the 4.67μ band to work with.

As shown in FIG. 5, the fire detector comprises four main parts. They are respectively a re-entrant "waveguide" sample chamber 3, an adjoining heat exchanger 4, an infrared components assembly 5 which houses both the infrared source 9 and detector 10 side by side and a printed circuit board (PCB) 6 housing the signal processing electronics. The sample chamber 3 is of a re-entrant design. By that I mean the source 9 and the detector 10 are both located on the same end 7 of a wave guide or tube sample chamber as shown in FIG. 5. Thus the radiation emanating from the source 9 bounces back from a reflective surface 8 at the other end before being detected by the detector 10. The obvious advantage of the re-entrant design is the effective doubling for the path length when compared with the standard waveguide or tube sample chamber design.

Elongation of the sample chamber is important for all effluent gases generated by a fire especially CO. By operating the infrared source 9 at a very low temperature as compared with the standard practice of maximizing it, the modulation of the detector signal by the gas at or around 400° K would suffer. In order to compensate for this decrease in modulation, it is prudent to increase the path length of the sample chamber as much as possible.

In FIG. 5, the sample chamber 3 is thermally coupled to one end 7 of the infrared components assembly 5. An infrared detector 10, either of the thermopile or pyroelectric type, is installed at the center of the detector assembly 5 facing the reflective surface 8 at the far end of the sample chamber 3. When the effluent gas $H_2O$ is used in the design of the NDIR gas sensor fire detector, the infrared detector 10 uses a spectral filter having a CWL=6.27μ and FWHM=1.0μ as its hermetically sealed window. Similarly when the effluent gas CO is used in the design, a spectral filter having a CWL=4.67μ and FWHM=0.2μ is used instead. Side by side with the detector 10 is an active infrared source 9. The infrared source 9 is a small novel "semiconductor resistor" element fabricated on a very thin substrate such that a very small amount of input power (~0.2 W) that lasts for only a period of 10 msec. will be sufficient to raise its temperature to ~400° K.

The detector assembly 5 is in essence a highly polished (ε~0.03) aluminum cylinder approximately one inch in diameter and one inch in length with one end 11 opened to accommodate the infrared source 9 and detector 10. The other end 12 is opened and shaped as a conical mirror for matching the aperture opening end 13 of the re-entrant sample chamber 3 (see FIG. 5). Sample chamber 3 is an aluminum waveguide or tubing type with both its inside and outside surfaces, including the reflective surface 8 at one end, highly polished. Since the sample chamber 3 and the detector assembly 5 are thermally coupled together, their temperatures are very close to one another at all times.

As shown in FIG. 5, the heat exchanger 4 is adjoining the sample chamber 3. In actuality, both are made out of one piece of aluminum as illustrated in FIG. 6. As shown in FIG. 6, the sample chamber 3 and the heat exchanger 4 are extruded out of aluminum with both the internal and external surfaces highly polished during the extrusion process. By fabricating them this way, air can get in the heat exchanger 4 through holes 14 (see FIG. 5) and exit through holes 15. When the effluent gas used is either $CO_2$ or CO in the current fire detector design, the holes 14 are covered with thin pieces of polyethylene film 16 so as to protect the inside of the sample chamber 3 from the invasion of dust, dirt and water vapor. When the effluent gas is $H_2O$, a Gore™ membrane is used in lieu of the polyethylene film 16 in order to let $H_2O$ and gas molecules through but repel dust and smoke particles from entering. Any ambient gas, including the three principal effluent ones from a fire, must first diffuse through the heat exchanger 4 before entering the sample chamber 3. As the name implies, the function of the heat exchanger 4 is to cool and lower the temperature of the effluent gases prior to its entrance into the sample chamber 3 for more efficient detection in view of the Law of Detailed Balance.

From FIG. 5 it is clear that in order to take advantage of using an aluminum extrusion process in the fabrication of the re-entrant sample chamber 3 and the adjoining heat exchanger 4 together, second operations on the extruded part are needed to complete the fire detector design. First, the reflective surface 8 at the end of the sample chamber 3 away from the infrared components assembly 5 must be fabricated separately and then installed in place. Also the end caps 17 and 18 for the heat exchanger 4 must also be fabricated separately and then installed in place. Finally, the sets of holes 15 along the sample chamber 3 and the set 14 along the heat exchanger 4 must also be machined separately in order to complete the fabrication for the fire detector.

As mentioned earlier, when the NDIR gas sensor fire detector is designed using the effluent gas $H_2O$ from fire, additional precaution must be taken in the design in order to avoid the condensation of $H_2O$ inside the heat exchanger 4 and the sample chamber 3. If such precautions are not properly taken, the concentration of $H_2O$ gas or water vapor from a fire might fluctuate uncontrollably making any fire detection algorithm unreliable and therefore prone to possible failure to enunciate fires. In order to prevent any water vapor condensation inside the heat exchanger 4 and sample chamber 3, the inside and outside of both of them can be coated with an UV-activated hydrophobic oligomer film such as CN301 (polybutadiene dimethacrylate). Polybutadiene dimethacrylate is a low viscosity, flexible, hydrophobic oligomer with excellent mechanical properties. Additionally, cured films of CN301 resist acids, alkali and high humidity.

When the effluent gas CO from a fire is used to design an NDIR gas sensor fire detector, no particular precautions need to be taken except to compensate for its weak absorption band at $4.67\mu$. This could be accomplished by extending the path length of the sample chamber without compromising the power consumption for the fire detector.

The present design of the NDIR gas sensor, deployed as a low power, low cost, fast responding and false-alarm resistant fire detector, follows the basic guidelines demanded by the Law of Detailed Balance. To the extent that a particular absorption band chosen for a particular effluent gas generated by a fire is selected for the fire detector in order to lower the demand for the operating temperature of the infrared source, thereby reducing the amount of power required to operate the fire detector, there is a built-in leeway that would allow the operating temperature of the source to be raised in order to overcome the limitation imposed by the Law of Detailed Balance. For example, if a 3-Volt 10 msec. pulse is used to raise the temperature of the source to say 400° K or 100° C., and it is found that there is insufficient S/N to run the fire detector, one can extend the turn-on time of the source to beyond 10 msec., at the expense of using more power but enable the source to be operated at a higher temperature and thereby providing an adequate S/N to get the job done. This built-in leeway is best used with a smart fire algorithm for the fire detector to optimally detect the onset of fires. This leeway would only be used when there is a need at a particular time during the fire to ascertain accurately the concentration of a particular effluent gas or its rate of rise. However, during the time when the fire detector is on sentinel, such an increase of power will not be needed in order to save power.

Although lowering the power consumption of the presently invented NDIR gas sensor fire detector is of the primary importance, its unit production cost is equally important and cannot be simply ignored. Since labor is the most significant and frequently the non-wielding part of an NDIR gas sensor cost, one simply cannot afford the treatment of the present NDIR fire detector as a regular gas sensor which must be calibrated prior to its use. Instead, one must rely on the sudden concentration level increase of an affluent gas or its rate of rise together with a concomitant rise in temperature around the fire detector as a way to develop the viable fire algorithms for enunciating the onset of fires.

It is clear that when an NDIR gas sensor does not require a reference channel (i.e. a single-beam instead of double-beam implementation) for its operation and also does not need to be calibrated to function as a fire detector, the sensor circuit will be very much simplified and its production cost will also be greatly reduced. Thus the presently invented ultra low power NDIR gas sensor affords very low power consumption in addition to very low cost. Although the gas sensor of the present invention can be employed by itself as a standalone fire detector, it can also be combined, if desired, with other smoke detectors as already been well taught in prior art.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A fire detector, comprising:
an NDIR sensor that generates a detector signal based upon an active source and at least one absorption band selected from the group consisting of a $15.1\mu$ absorption band of $CO_2$, a $6.27\mu$ absorption band of $H_2O$ and a $4.67\mu$ absorption band for CO; and a signal processor which receives the detector signal and generates an alarm signal to warn of a fire when a preselected criterion is met;

wherein the NDIR sensor is comprised of:
- a waveguide sample chamber with at least one opening covered by a thin filtering membrane that allows $CO_2$ and $H_2O$ molecules to diffuse freely into and out of the sample chamber but rejects dust and smoke particles from entering the sample chamber;
- a heat exchanger thermally connected to the sample chamber with at least one opening covered by at least one second thin filtering membrane that allows preselected molecules to diffuse freely into and out of the heat chamber but rejects dust and smoke particles from entering the heat exchanger; and
- an infrared components assembly that houses the active source and a detector which is thermally coupled to an end of the sample chamber; and wherein the at least one absorption band is the 6.27µ absorption band of $H_2O$, the at least one second thin filtering membrane allows $H_2O$ molecules to pass through it and inside surfaces of both the sample chamber and the heat exchanger are coated with a hydrophobic coating to prevent condensation of $H_2O$ molecules.

2. The fire detector of claim 1, wherein the signal processor relies upon a detection algorithm that is based upon a sudden drop of the detector output signal indicative of the onset of a fire.

3. The fire detector of claim 2, wherein the detector signal drop is excess of 20% from the then prevailing signal level.

4. The fire detector of claim 1, the sample chamber and the heat exchanger are integrally formed out of aluminum and the sample chamber is of a reentrant design.

5. The fire detector of claim 1, wherein the detector signal is based upon two or more of the absorption bands selected from the group consisting of the 15.1µ absorption band of $CO_2$, the 6.27µ absorption band of $H_2O$ and the 4.67µ absorption band for CO.

6. The fire detector of claim 1, wherein the signal processor utilizes synchronized signal processing from the detector signal.

7. The fire detector of claim 6, wherein the signal processor relies upon a detection algorithm that is based upon a synchronized output signal representative of gas concentration of at least one of the gasses selected from the group consisting of CO, $CO_2$ and $H_2O$.

8. The fire detector of claim 1, wherein the $CO_2$ sensor is used as a standalone smoke detector.

9. The fire detector of claim 1, wherein the $CO_2$ sensor is combined with a smoke detector.

10. A method for generating an alarm signal in response to a fire, comprising the steps of:
- using a NOIR sensor with an active source to generate a detector signal based upon at least one absorption band selected from the group consisting of a 15.1µ absorption band of $CO_2$, a 6.27µ absorption band of $H_2O$ and a 4.67µ absorption band for CO; and
- generating the alarm signal when a preselected criterion indicative of the onset of a fire is met based upon an analysis of the detector signal;
- wherein the detector signal is based upon two or more of the absorption bands selected from the group consisting of the 15.1µ absorption band of $CO_2$, the 6.27µ absorption band of $H_2O$ and the 4.67µ absorption band for CO.

11. The method of claim 10, wherein the analysis of the detector signal is performed by using a detection algorithm that relies upon a trending pattern of the detector signal.

12. The method of claim 10, wherein the trending pattern includes a substantial drop in the detector signal strength when a species that is the subject of the at least one absorption band subsequently arrives near the sensor as the fire persists.

13. The method of claim 12, wherein the analysis of the detector signal is performed by using a detection algorithm that analyzes the synchronized output signal.

* * * * *